United States Patent
Mane et al.

(10) Patent No.: US 11,065,334 B2
(45) Date of Patent: Jul. 20, 2021

(54) BORON-10 CONTAINING BIOCOMPATIBLE NANOSTRUCTURES

(71) Applicant: UCHICAGO ARGONNE, LLC, Chicago, IL (US)

(72) Inventors: Anil U. Mane, Naperville, IL (US); Jeffrey W. Elam, Elmhurst, IL (US)

(73) Assignee: UChicago Argonne, LLC, Chicago, IL (US)

(*) Notice: Subject to any disclaimer, the term of this patent is extended or adjusted under 35 U.S.C. 154(b) by 0 days.

(21) Appl. No.: 16/190,011

(22) Filed: Nov. 13, 2018

(65) Prior Publication Data

US 2020/0147218 A1 May 14, 2020

(51) Int. Cl.
| | |
|---|---|
| *B82Y 40/00* | (2011.01) |
| *B82Y 5/00* | (2011.01) |
| *A61K 41/00* | (2020.01) |
| *C07F 5/02* | (2006.01) |

(52) U.S. Cl.
CPC .......... *A61K 41/0095* (2013.01); *C07F 5/027* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 8,956,983 B2 * | 2/2015 | Swaminathan | ... H01L 21/76898 438/763 |
| 2005/0180917 A1 | 8/2005 | Patel | |

OTHER PUBLICATIONS

Zhu Y, Lin Y, Zhu YZ, Lu J, Maguire JA, Hosmane NS. Boron drug delivery via encapsulated magnetic nanocomposites: a new approach for BNCT in cancer treatment. Journal of Nanomaterials. 2010;2010. (Year: 2010).*

Akbar A, Riaz S, Hussain SS, Atiq S, Xu YB, Naseem S. Systematic Magnetic and Dielectric Investigations of Aluminum Doped Iron Oxide Thin Films. The 2016 World Congress on Advances in Civil, Environmental and Materials Research (ACEM16) Jeju Isalnd, KOrea, Aug. 28-Sep. 1, 2016 (Year: 2016).*

Knez M, Nielsch K, Niinistö L. Synthesis and surface engineering of complex nanostructures by atomic layer deposition. Advanced Materials. Nov. 5, 2007;19(21):3425-38. (Year: 2007).*

Wang X, Krommenhoek PJ, Bradford PD, Gong B, Tracy JB, Parsons GN, Luo TJ, Zhu YT. Coating alumina on catalytic iron oxide nanoparticles for synthesizing vertically aligned carbon nanotube arrays. ACS applied materials & interfaces. Nov. 23, 2011;3(11):4180-4. (Year: 2011).*

Garcia-Alonso D, Potts SE, van Helvoirt CA, Verheijen MA, Kessels WM. Atomic layer deposition of B-doped ZnO using triisopropyl borate as the boron precursor and comparison with Al-doped ZnO. Journal of Materials Chemistry C. 2015;3(13):3095-107. (Year: 2015).*

(Continued)

*Primary Examiner* — Nissa M Westerberg
(74) *Attorney, Agent, or Firm* — Foley & Lardner LLP (57) ABSTRACT

A method comprises providing a plurality of nanostructures comprising a base material. The plurality of nanostructures are exposed to a first material at a first deposition temperature. The plurality of nanoparticles are exposed to a second material at a second deposition temperature, and exposed to a Boron-10 ($^{10}B$) containing material at a third deposition temperature so as to form a $^{10}B$-metal oxide based composite nanostructure.

4 Claims, 11 Drawing Sheets

(56) References Cited

OTHER PUBLICATIONS

Barth, et al., "Boron Neutron Capture Therapy of Cancer: Current Status and Future Prospects," Clinical Cancer Research 11(11), pp. 3987-4002 (2005).

Finch, et al., "Biocompatibility of atomic layer-deposited alumina thin films," Journal of Biomedical Materials Research Part A 87A(1), pp. 100-106 (2008).

Lyer, et al., "Visualisation of Tumour Regression after Local Chemotherapy with Magnetic Nanoparticles—A Pilot Study," Anticancer Research 30(5), pp. 1553-1557 (2010).

Tietze, et al., "Quantification of drug-loaded magnetic nanoparticles in rabbit liver and tumor after in vivo administration," Journal of Magnetism and Magnetic Materials 321(11), pp. 1465-1468 (2009).

* cited by examiner

BORON-10 CONTAINING BIOCOMPATIBLE NANOSTRUCTURES

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to the field of Boron-10 ($^{10}$B) containing composite nanostructures formed using Atomic Layer Deposition (ALD).

BACKGROUND

Boron neutron capture therapy (BNCT) is a binary method for the treatment of cancer, which is based on the nuclear reaction between boron atoms and low-energy thermal neutrons. In the naturally occurring state, elemental boron has two stable isotopes, namely boron-10 ($^{10}$B) and boron-11 ($^{11}$B). The more abundant isotope is $^{11}$B (around 80%), however, the most distinguishing property of $^{10}$B is its high neutron capture cross section for thermal neutrons (also called as slow neutrons). Hence, the reaction of a neutron with $^{10}$B yields two charged particles, a $^4$He nucleus and a $^7$Li nucleus, each of which is able to kill tumor cells due to their high linear energy transfer. For successful BNCT, a minimum of 20-30 μg of nonradioactive $^{10}$B per gram of tumor tissue is generally used. Another factor for the success of BNCT is the selective delivery of high amounts of boronated compounds to tumor cells, while at the same time, the boron concentration in the cells of surrounding normal tissue should be kept low to minimize the damage to normal tissue.

Further BNCT has been under study in cancer research to offer a much more targeted therapy compared to existing chemo or radiotherapy. The success of BNCT strongly depends on the improvement of the selectivity of boron-labeled compounds for cancer tissues (at least 20 ppm $^{10}$B in the tumor is desirable) in order to establish a sufficient dose ratio between tumor cells, and healthy tissues (at least 3:1), e.g., blood vessels and normal brain cells, during a sufficient time span. In addition to that, a high neutron flux density of about $10^9$ neutrons/s cm$^2$ is desirable. The attainable absolute concentration and enrichment of $^{10}$B in tumor cells strongly depends on the method of application and in the studies performed so far, $^{10}$B levels only reached the minimum values necessary for this kind of tumor therapy. In spite of all efforts, a more effective boron delivery agent is highly desirable in order to perform targeted and reliable BNCT delivery to tumorous and cancerous cells.

SUMMARY

Embodiments described herein relate generally to composite nanostructures including $^{10}$B, methods of forming such composite nanostructures using ALD, and using such composite nanostructures for treating cancer.

In some embodiments, a method comprises providing a plurality of nanostructures comprising a base material; exposing the plurality of nanostructures to a first material at a first deposition temperature; exposing the plurality of nanostructures to a second material at a second deposition temperature; and exposing the plurality of nanostructures to a 10-Boron ($^{10}$B) containing material at a third deposition temperature so as to form a $^{10}$B-metal oxide-based composite nanostructure.

In some embodiments, a composite nanostructure comprises a first layer forming a core of the composite nanostructure, the first layer comprising a base material. A second layer of a $^{10}$B-metal oxide composite is deposited on the first layer.

In some embodiments, a method of treating cancer comprises injecting a plurality of composite nanostructures comprising $^{10}$B-metal oxide-magnetic material into a blood stream of a patient having cancer cells. A magnetic field is generated in a vicinity of the cancer cells so as to accumulate at least a portion of the plurality of composite nanostructures in the vicinity of the cancer cells. At least the portion of the plurality of composite nanostructures is irradiated with a stream of epithermal neutrons.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Embodiments described herein relate generally to composite nanostructures including $^{10}$B, methods of forming such composite nanostructures using ALD, and using such composite nanostructures for treating cancer.

Boron neutron capture therapy (BNCT) is a binary method for the treatment of cancer, which is based on the nuclear reaction between boron atoms and low-energy thermal neutrons. A promising strategy for targeted delivery of boron to tumorous or cancerous tissues is the use of magnetically directed nanoparticles. The concept of Magnetic Drug Targeting (MDT), an efficient tumor treatment strategy, implies intra-arterially administered superparamagnetic iron oxide nanoparticles (SPIONs), which are attracted by an external magnetic field that is directed to the tumor tissue. However, fabrication of stable $^{10}$B containing magnetic nanoparticles using conventional processes is difficult.

Embodiments described herein relate to a method to create isotopically pure $^{10}$B containing composite layers which can be added on to nanoparticle (e.g., biocompatible nanoparticles) substrates to form $^{10}$B composite nanostructures. For example, $^{10}$B-metal oxide nanocomposites can be deposited on a nanoparticle based base material template such as Fe$_2$O$_3$, Al$_2$O$_3$, TiO$_2$, SiO$_2$, Au, fullerenes etc., or soft biocompatible polymeric material and/or biocompatible magnetic materials (e.g., FeO or Fe$_2$O$_3$ etc.).

Various embodiments of the $^{10}$B-metal oxide-base material composite nanostructures and methods to form such nanostructures may provide one or more benefits including, for example: (1) allowing precise control of loading of $^{10}$B in the nanostructures; (2) allowing fabrication of nanostructures using a low cost and easily scalable ALD process; (3) providing fabrication of uniform and conformal coatings of $^{10}$B-metal oxide on the base material; (4) allowing fabrication at temperatures as low as room temperature; (5) allowing fabrication of biocompatible nanostructures that can be inserted safely in an animal or human body and be used as a therapeutic agent such as in cancer treatment.

Figure 1:
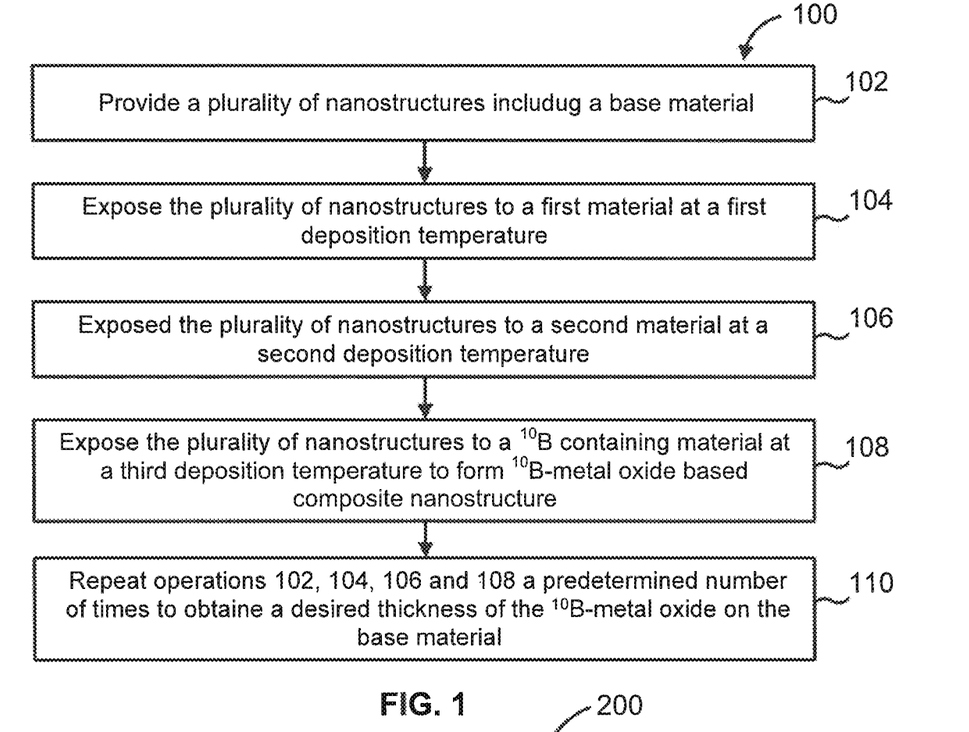
FIG. 1 is schematic flow diagram of a method for fabricating composite nanostructures including $^{10}$B, according to an embodiment.

FIG. 1 is a schematic flow diagram of a method 100 for fabricating a boron containing composite nanostructure such as a boron-metal oxide-base material composite nanostructure, according to an embodiment. The method 100 includes providing a plurality of nanostructures including a base material, at 102. The nanostructures may have any suitable size range, for example, in a range of 5-500 nm, inclusive of all ranges and values therebetween. The base material may include, for example, Al$_2$O$_3$, Fe$_2$O$_3$, ZrO$_2$, SiO$_2$, organically modified silica (ORMOSIL), TiO$_2$, MgO, CaF$_2$, ZnO, Au, Ag, graphene, graphene oxide, NaCl or KCl. In various embodiments, the base material may be a biocompatible material, for example, any of the base materials described herein. In some embodiments, the base material may include a polymer (e.g., a biocompatible polymer such as a biodegradable polymer) which is capable of withstanding high temperature deposition (e.g., in a range of 50-200 degrees Celsius) of a $^{10}$B containing composite thereon. Such polymers may include, for example, polyamides, polycarbonates, polyurethanes, poly(glycolic acid), polylactides, poly(a-esters), poly(ethylene glycol), poly(lactide-co-glycolide), polyhydroxyalkanoates, polycaprolactones, polypropylene fumarate, polyanhidrides, polyacetals, poly(ortho esters), polycarbonates, polyphosphazenes, polyphosphoesters, polyethers, etc. In particular embodiments, the base material may include a magnetic material (e.g., FeO or Fe$_2$O$_3$).

In some embodiment, the plurality of nanostructures may be formed entirely of the base material. In some embodiments, the plurality of nanostructures including the base material may be formed using an ALD process or any other suitable deposition process and may include a substrate material having a layer of the base material disposed thereon. For example, a plurality of nanoparticles may be provided as a substrate, and the base material grown on a surface thereof via ALD, chemical vapor deposition (CVD), metal oxide CVD (MOCVD), plasma enhanced CVD (PECVD), sputtering, e-beam evaporation or any other suitable deposition process so as to form the plurality of nanostructures.

In some embodiments, the base material may be grown on the substrate material via ALD which may be performed in a reaction chamber. ALD processes often comprise two half-reactions, whereby precursor materials for each half-reaction are kept separated throughout the coating process. ALD material growth is based on self-limiting surface reactions, which makes achieving atomic scale deposition control possible. In a first half-reaction, a precursor gas is introduced to a substrate surface and produces a first monolayer. Excess or unreacted species and/or reaction by-product from the first half-reaction may be purged from the substrate surface by flow of inert gas (i.e. nitrogen, argon, etc.), vacuum evacuation, by moving the substrate into a zone of pure inert gas (i.e. spatial ALD) or other similar removal techniques. A second precursor of gas is then introduced to the substrate surface and reacts with the first monolayer to produce a monolayer on the substrate surface (i.e., the surface of the plurality of nanoparticles). Excess or unreacted species and/or reaction by-product from the second half-reaction may be purged from the deposition chamber using similar evacuation methods as used for the excess or unreacted species and/or reaction by-product from the first half-reaction.

In some embodiments, providing the base material may include exposing the plurality of nanoparticles to a first base material precursor at a fourth deposition temperature exposure to the plurality of nanoparticles to a second base material precursor, at a fifth deposition temperature. Exposing of plurality of nanoparticles to the first and second base material precursor may be performed in an ALD reaction chamber and together comprise an ALD cycle. For example, a plurality of nanoparticles formed from any suitable substrate material may be provided and a predetermined number of ALD cycles including exposure to the first and second base material precursors may be performed to deposit a layer of the base material having a predetermined thickness thereon, so as to form the plurality of nanostructures that include the base material. Each of the fourth and fifth deposition temperatures may be in a range of 100-300 degrees Celsius, inclusive of all ranges and values therebetween. In other embodiments, the fourth and fifth deposition temperatures may be in a range of room temperature to 100 degrees Celsius. In some embodiments, a deposition pressure during the first and second base material precursor exposures may be in range of several mTorr to 1000 Torr.

In some embodiments, the base material may include $Al_2O_3$ or any other aluminum containing base material. In such embodiments, the first base material precursor may include an aluminum containing precursor including at least one of trimethylaluminum ($Al(CH_3)_3$) (TMA), triethylaluminum (($C_2H_5)_3Al$) (TEA), triethyl(tri-sec-butoxy)dialuminum (($C_2H_5)_3Al_2(OC_4H_9)_3$), aluminum chloride ($AlCl_3$), aluminum isopropoxide ($Al((OCH(CH_3)_2)_3)$), dimethylaluminum isopropoxide (($CH_3)_2AlOCH(CH_3)_2$), tris(2,2,6,6-tetramethyl-3,5-heptanedionato)aluminum ($(ARTMHD)_3$), tri-isobutylaluminum (($C_4H_9)_3Al$), aluminum hexafluoroacetylacetonate ($Al(CF_3COCHCOCF_3)_3$), aluminum ethoxide ($Al(OC_2H_5)_3$), aluminum s-butoxide ($Al(OC_4H_9)_3$), or aluminum acetylacetonate ($Al(CH_3COCHCOCH_3)_3$). Furthermore, the second base material precursor may include an oxygen containing precursor such as, for example, at least one of water ($H_2O$), ozone ($O_3$), hydrogen peroxide ($H_2O_2$), or oxygen ($O_2$). The number ALD cycles of the first and second base material precursors may be selected based on a desired thickness of the base material on the nanoparticle surface.

In other embodiments, the base material may include $TiO_2$ or any other titanium containing base material. In such embodiments, the first base material precursor may include a titanium containing precursor comprising at least one of titanium tetraisopropoxide, titanium tetrachloride, titanium tetraiodide, tetrakis dimethylamino titanium, tetrakis diethylamino titanium, tetrakis ethyl-methylamino titanium, titanium phenyltriisopropoxide, titanocene dichloride, methyltitanium trichloride and methyltriisopropoxytitanium, and the second base material precursor may include an oxygen containing precursor, as previously described herein.

In still other embodiments, the base material may include FeO, $Fe_2O_3$ or any other iron containing base material. In such embodiments, the first base material precursor may include an iron contain precursor, for example, $Fe(Cp)_2$ $FeCl_3$, tris(2,2,6,6-tetramethyl-3,5-heptanedionato) Fe(III), or an iron amidinate, and the second base material precursor may include an oxygen containing precursor, as previously described herein.

In yet other embodiments, the first base material precursor may include diethyl zinc, dimethyl zinc, diphenyl zinc, bis(pentafluorophenyl)zinc, bis(2,2,6,6-tetramethyl-3,5-heptanedionato)zinc(II), tetramethyl tin, molybdenumhexacarbonyl, Bis(cyclopentadienyl)magnesium(II), bis(cyclopentadienyl)zirconium(IV) dihydride 95%, zirconium(IV) dibutoxide(bis-2,4-pentanedionate), zirconium(IV) 2-ethylhexanoate or any other suitable metal containing precursor.

At 104, the plurality of nanostructures are exposed to a first material at a first deposition temperature, for example, in an ALD reaction chamber. The first deposition temperature may be in a range of 100-300 degrees Celsius. A first deposition pressure may be in range of several mTorr to 1000 Torr. In other embodiments, the first deposition temperature may be in a range from room temperature to 100 degrees Celsius. In some embodiments, it may be desirable for the boron containing composite nanostructure to include aluminum. In such embodiments, the first material may include an aluminum containing material, which may form a first monolayer of aluminum on the surfaces of the plurality of nanoparticles. In some embodiments, the aluminum containing material may be trimethylaluminum ($Al(CH_3)_3$) (TMA), triethylaluminum (($C_2H_5)_3Al$) (TEA), triethyl(tri-sec-butoxy)dialuminum (($C_2H_5)_3Al_2(OC_4H_9)_3$), aluminum chloride ($AlCl_3$), aluminum isopropoxide ($Al((OCH(CH_3)_2)_3)$), dimethylaluminum isopropoxide (($CH_3)_2AlOCH(CH_3)_2$), tris(2,2,6,6-tetramethyl-3,5-heptanedionato)aluminum ($(ARTMHD)_3$), tri-isobutylaluminum (($C_4H_9)_3$ Al), aluminum hexafluoroacetylacetonate ($Al(CF_3COCHCOCF_3)_3$), aluminum ethoxide ($Al(OC_2H_5)_3$), aluminum s-butoxide ($Al(OC_4H_9)_3$), or aluminum acetylacetonate ($Al(CH_3COCHCOCH_3)_3$). After operation 104, any remaining first material is purged from the reaction chamber in which the ALD cycles are being performed, for example, by flowing a suitable inert gas such as argon or nitrogen into the reaction chamber.

In other embodiments, it may be desirable for the boron containing composite nanostructure to include titanium. In such embodiments, the first material may include a titanium containing precursor comprising at least one of titanium tetraisopropoxide, titanium tetrachloride, titanium tetraiodide, tetrakis dimethyl amino titanium, tetrakis di ethyl amino titanium, tetrakis ethyl-methylamino titanium, titanium phenyltriisopropoxide, titanocene dichloride, methyltitanium trichloride and methyltriisopropoxytitanium.

In still other embodiments, it may be desirable for the boron contain composite nanostructure to include iron (e.g., to obtain a magnetic boron containing composite nanostructure). In such embodiments, the first material may include $Fe(Cp)_2$, $FeCl_3$, tris(2,2,6,6-tetramethyl-3,5-heptanedionato) Fe(III), an iron amidinate, or any other suitable iron containing material.

In yet other embodiments, the first material may include diethyl zinc, dimethyl zinc, diphenyl zinc, bis(pentafluorophenyl)zinc, bis(2,2,6,6-tetramethyl-3,5-heptanedionato) zinc(II), tetramethyl tin, molybdenumhexacarbonyl, Bis(cyclopentadienyl)magnesium(II), bis(cyclopentadienyl) zirconium(IV) dihydride 95%, zirconium(IV) dibutoxide (bis-2,4-pentanedionate), zirconium(IV) 2-ethylhexanoate or any other suitable metal containing material.

At 106, the plurality of nanostructures are exposure to a second material at a second deposition temperature, for example, in an ALD reaction chamber. For example, the first monolayer formed on the surface of each of the plurality of nanoparticles may include a metal and it may be desirable for the boron containing composite nanostructure to include a metal oxide. In such embodiments, the second precursor material includes an oxygen containing material which reacts with the metallic first monolayer to form a metal oxide monolayer. In various embodiments, the oxygen containing material may be water ($H_2O$). In other embodiments, the oxygen containing material may comprise at least one of ozone ($O_3$), hydrogen peroxide ($H_2O_2$), or oxygen ($O_2$). In some embodiments, the oxygen containing material may consist of a first oxygen containing material and the first monolayer may be exposed (e.g., after an intermediate purge cycle), to a second oxygen containing material. The second deposition temperature may be in a range of 100-300 degrees Celsius. In other embodiments, the second deposition temperature may be in a range of room temperature to 100 degrees Celsius. Furthermore, a second deposition pressure may be in range of several mTorr to 1000 Torr. In some embodiments, the metal oxide layer may include the same material as the base material. In other embodiments, the metal oxide layer may be formed from a different material than the base material. After operation 106, any remaining second precursor is purged from the reaction chamber in which the ALD cycles are being performed, for example, by flowing a suitable inert gas such as argon or nitrogen into the reaction chamber.

At 108, the plurality of nanostructures are exposed to a $^{10}$B containing material at a third deposition temperature to form $^{10}$B-metal oxide-based composite nanostructure (also referred to herein as "the boron composite nanostructure"), for example, in the ALD reaction chamber. For example, the boron containing material reacts with the metal oxide monolayer formed on the base material to form the boron composite nanostructure. The $^{10}$B containing material may include at least one of boric acid ($BH_3O_3$), trimethyl borate (TMB) ($C_3H_9BO_3$), triethyl borate (TEB) ($C_6H_{15}BO_3$), boron tribromide ($BBr_3$), boron trifluoride ($BF_3$), diboron tetrafluoride ($B_2F_4$), triisopropylborane (($C_3H_7)_3B$), triethoxyborane (($C_2H_5O)_3B$), or triisopropoxyborane (($C_3H_7O)_3B$). The boron containing materials disclosed herein may be enriched with $^{10}$B isotopic elements. The third deposition temperature may be in a range of 100-300 degrees Celsius. In other embodiments, the third deposition temperature may be in a range of room temperature to 100 degrees Celsius. Furthermore, a third deposition pressure may be in range of several mTorr to 1000 Torr. After operation 108, any remaining third precursor is purged from the reaction chamber in which the ALD cycles are being performed, for example, by flowing a suitable inert gas such as argon or nitrogen into the reaction chamber.

In some embodiments, the $^{10}$B precursor material may also include a $C_1$-$C_6$ alcohol compound (e.g., methanol, ethanol, isopropyl alcohol, etc.). For example, the $^{10}$B containing material (e.g., a borate or boric acid) dissolved or suspended in the $C_1$-$C_6$ alcohol compound, or the $^{10}$B containing material may be introduced into the reaction chamber simultaneously with a $C_1$-$C_6$ alcohol compound. In some embodiments, the $^{10}$B containing material may be introduced into the reaction chamber prior to the alcohol compound and after purging of the excess first material and reaction by-product of the first half-reaction. In some embodiments, the $^{10}$B containing material may be introduced into the reaction chamber after the alcohol compound. In some embodiments where the $C_1$-$C_6$ alcohol compound is present, carbon comprises a minor impurity in the system, with the major component being $^{10}$B in a metal oxide-base material composite. In particular embodiments, the $C_1$-$C_6$ alcohol may also serve as the oxygen containing precursor such that operation 106 may be excluded.

In some embodiments, the operation 108 may include a first sub-step of reacting the first monolayer with the boron containing material followed by purging excess boron containing material and reaction by-product from the system and a second sub-step of reacting the boron containing surface with the oxygen containing precursor followed by purging excess oxygen containing precursor and reaction by-product from the system. In such embodiments, operation 106 may be excluded.

In some embodiments, the operation 108 may include a first sub-step of reacting the oxygen containing surface with the boron containing material, followed by a second sub-step of purging excess oxygen containing precursor, excess boron containing material, and reaction by-product from the reaction chamber (e.g., by purging the reaction chamber with $N_2$, argon or any other inert gas). In other embodiments, the operation 108 may include a first sub-step of reacting the first monolayer with the boron containing material, followed by a second sub-step of reacting the boron containing surface with the oxygen containing material, followed by a third sub-step of purging excess boron containing material, excess oxygen containing material, and reaction by-product from the system. In such embodiments, operation 106 may be excluded.

In some embodiments, operations 104, 106, and 108 may be performed any suitable number of times selected to obtain a desired thickness of the $^{10}$B-metal oxide layer on the base material. For example, operations 104, 106 and 108 may together form an ALD cycle. In such embodiments, any number of ALD cycles may be performed to obtain a desired thickness of the $^{10}$B-metal oxide layer on the base material. For example, operations 104, 106 and 108 may be repeated a predetermined number of times, at 110, to obtain a desired thickness of the $^{10}$B-metal oxide layer on the base material.

In some embodiments in which the first precursor material includes an aluminum containing material, the $^{10}$B-metal oxide-based composite nanostructure comprises $^{10}$B$_x$—$Al_yO_z$-base material, where x>0, y>0 and z>0. For example, the boron composite nanostructure may include $^{10}$B—AlO-base material or $^{10}$B—$Al_2O_3$-base material composite nanostructure. In other embodiments, the $^{10}$B-metal oxide-based composite nanostructure includes $^{10}$B$_x$—$Al_{2-x}O_3$-base material, where x is greater than 0 and less than 2.

In other embodiments in which the first precursor material includes a titanium containing material, the $^{10}$B-metal oxide-based composite nanostructure comprises $^{10}$B$_x$—$Ti_yO_z$-base material, where x>0, y>0 and z>0. For example, the boron composite nanostructure may include $^{10}$B—TiO-base material or $^{10}$B—$TiO_2$-base material.

In some embodiments, the $^{10}$B$_x$—$Al_yO_z$-base material may include an oxygen concentration in the range of 40 atomic % to 70 atomic %. In some embodiments, the $^{10}$B$_x$—$Al_yO_z$-base material may comprise an oxygen concentration in the range of 50 atomic % to 60 atomic %. In some embodiments, the $^{10}$B$_x$—$Al_yO_z$-base material may comprise an aluminum concentration in the range of 15 atomic % to 50 atomic %. In some embodiments, the $^{10}$B$_x$—$Al_yO_z$-base material may comprise an aluminum concentration in the range of 25 atomic % to 40 atomic %. Precision-controlled atomic percentage of boron may also be achieved in the composite films. In some embodiments, the $^{10}$B x-$Al_yO_z$-base material may comprise a boron concentration in the range of 1 atomic % to 20 atomic %. In some embodiments, the $^{10}$B$_x$—$Al_yO_z$-base material may comprise a boron concentration in the range of 5 atomic % to 15 atomic %. In the example where x equals 1 (e.g., $^{10}$B—$AlO_3$ or $^{10}$B—$Al_2O_3$), the boron concentration is 20 atomic %. In some embodiments, the boron concentration may be approximately 40 atomic %.

Figure 2:
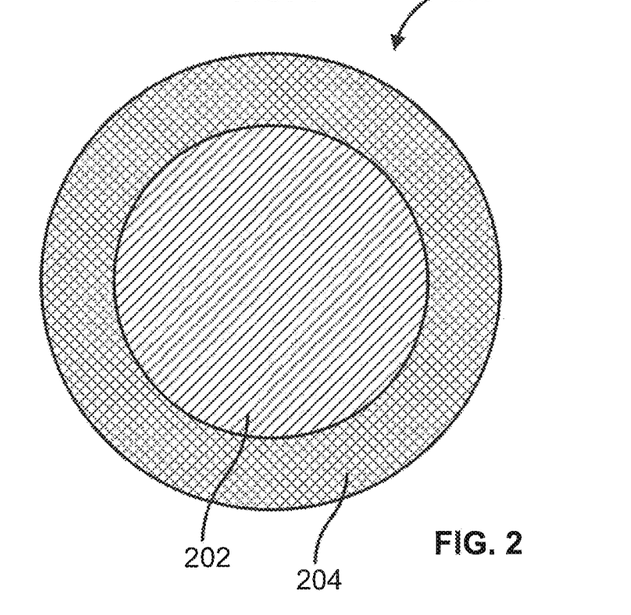
FIG. 2 is a schematic illustration of a $^{10}$B-metal oxide-base material composite nanostructure, according to an embodiment.

FIG. 2 is schematic illustration of a $^{10}$B-metal oxide-base material composite nanostructure 200, according to an embodiment. The composite nanostructure 200 comprises a first layer 202 forming a core of the nanostructure 200. The first layer 202 comprises a base material. In some embodiments, the base material includes at least one of $Al_2O_3$, $Fe_2O_3$, $ZrO_2$, $SiO_2$, organically modified silica (ORMOSIL), $TiO_2$, MgO, $CaF_2$, ZnO, Au, Ag, graphene, graphene oxide, NaCl or KCl, any other suitable base material or a combination thereof. In particular embodiments, the base material includes a magnetic material (e.g., FeO or $Fe_2O_3$). In some embodiments, the base material may include a polymer (e.g., a biocompatible polymer such as a biodegradable polymer), for example, polyamides, polycarbonates, polyurethanes, poly(glycolic acid), polylactides, poly (a-esters), poly(ethylene glycol), poly(lactide-co-glycolide), polyhydroxyalkanoates, polycaprolactones, polypropylene fumarate, polyanhidrides, polyacetals, poly(ortho esters), polycarbonates, polyphosphazenes, polyphosphoesters, polyethers, etc.

The composite nanostructure 200 also comprises a second layer 204 of a $^{10}$B-metal oxide composite deposited on the first layer 202 (e.g., via ALD as previously described herein). In some embodiments, the $^{10}$B-metal oxide composite may include a $^{10}$B$_x$—Al$_y$O$_z$, where x>0, y>0 and z>0. For example, the second layer 204 may include $^{10}$B—AlO or $^{10}$B—Al$_2$O$_3$. In other embodiments, the $^{10}$B-metal oxide-base material composite nanostructure includes $^{10}$B$_x$—Al$_{2-x}$O$_3$-base material, where x is greater than 0 and less than 2. In still other embodiments, the $^{10}$B-metal oxide includes $^{10}$B$_x$—Ti$_y$O$_z$-base material, where x>0, y>0 and z>0. For example, the second layer 204 may include $^{10}$B—TiO or $^{10}$B—TiO$_2$.

In some embodiments, any of the $^{10}$B-metal oxide-base material composite nanostructures described herein, for example, having a magnetic base material may be used for cancer therapy using boron-neutron capture therapy (BNCT).

Figure 3:
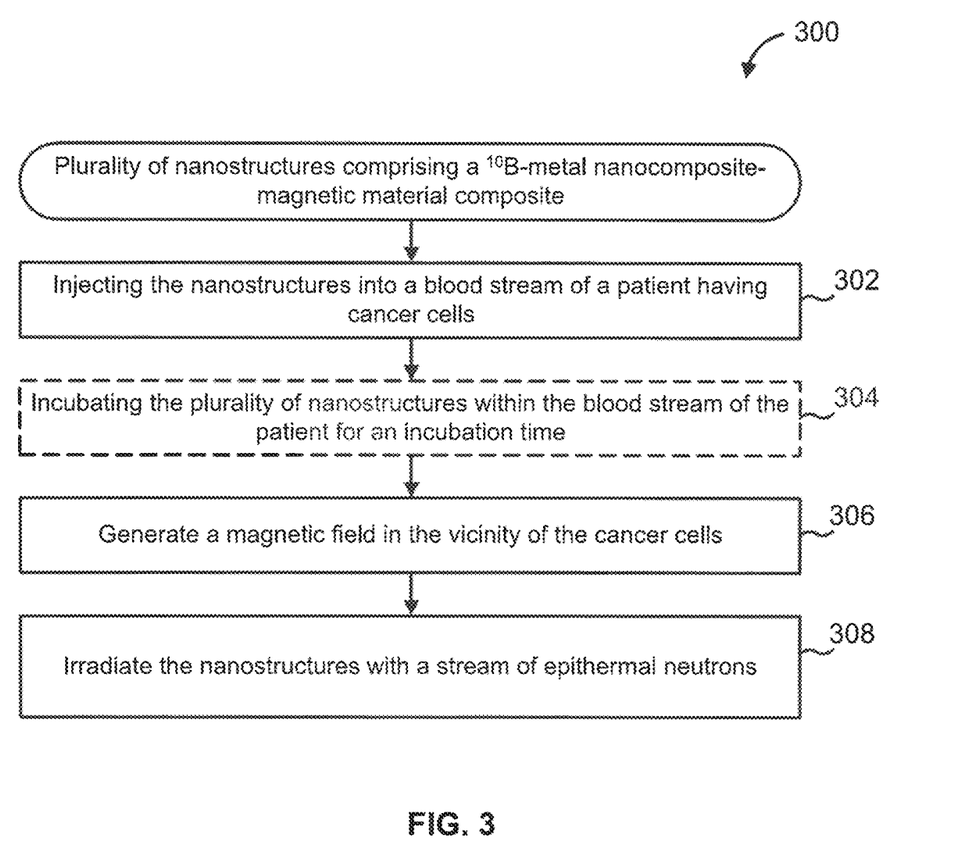
FIG. 3 is a schematic flow diagram of a method for treating cancer using $^{10}$B-metal oxide-magnetic material composite nanostructure, according to an embodiment.

For example, FIG. 3 shows a schematic flow diagram of a method 300 for treating cancer (e.g., colon cancer, lung cancer, stomach cancer, pancreatic cancer, brain cancer, tumors, cysts, etc.), according to an embodiment. The method 300 includes injecting a plurality of composite nanostructures comprising $^{10}$B-metal oxide-magnetic material composite into a blood stream of a patient having cancer cells, at 302. In such embodiments, the plurality of composite nanostructures may be administered intravenously into the blood stream of the patient. In other embodiments, the plurality of composite nanostructures may be administered orally to the patient. In some embodiments, the $^{10}$B-metal oxide-magnetic material composite may include $^{10}$B$_x$—Al$_y$O$_z$—Fe$_a$O$_b$ or $^{10}$B$_x$—Ti$_y$O$_z$—Fe$_a$O$_b$, where x>0, y>0, z>0, a>0 and b>0. For example, the $^{10}$B$_x$-metal oxide-magnetic material composite may include $^{10}$B—AlO—Fe$_2$O$_3$, $^{10}$B—Al$_2$O$_3$—Fe$_2$O$_3$, or $^{10}$B—TiO$_2$—Fe$_2$O$_3$. In other embodiments, the $^{10}$B-metal oxide-base material composite nanostructure includes $^{10}$B$_x$—Al$_{2-x}$O$_3$—Fe$_a$O$_b$, where x is greater than 0 and less than 2. The plurality of composite nanostructures may be dissolved or suspended in an appropriate carrier solution, for example, water, saline (e.g., phosphate buffered saline), biocompatible solvents, or any other suitable biocompatible carrier solution. In other embodiments in which oral delivery is desired, the plurality of composite nanostructures may be compounded in an oral solution, a tablet or a capsule.

In some embodiments, the method 300 also includes incubating the plurality of composite nanostructures within the blood stream of the patient for a predetermined incubation time, at 304. In various embodiments, the incubation time may be any suitable time or allowing the plurality of composite nanostructures to flow through the entire circulatory system of the patient, so as to allow sufficient time for at least a portion of the plurality of composite nanostructures to reach the cancer cells. In particular embodiments, the incubation time may include 10 mins, 20 mins, 40 mins, 1 hour, 2 hours, 3 hours or 4 hours inclusive of all ranges and values therebetween.

At 306, a magnetic field is generated in a vicinity of the cancer cells so as to accumulate at least a portion of the plurality of composite nanostructures in the vicinity of the cancer cells. In some embodiments, the magnetic field may be generated by a natural magnet positioned outside a body of patient proximate to a location of the cancer cells. In other embodiments, an electromagnet (e.g., a probe type electromagnet) may be used to generate an electromagnetic field in the vicinity of the cancer cells. In some embodiments, the magnetic field may be maintained in the vicinity of the cancer cells for a predetermined accumulation time (e.g., 10 minutes, 20 minutes, 30 minutes, 40 minutes, 50 minutes or 1 hour, inclusive of all ranges and values therebetween) so as to allow a larger portion of the plurality of composite nanostructures to accumulate in the vicinity of the cancer cells, as the plurality of nanoparticles travel through the circulatory system of the patient. In particular embodiments, the incubation time may be excluded and the accumulation time may be sufficient to allow plurality of nanoparticles to travel through the entire circulatory system of the patient as well as accumulation of least a portion of the plurality of composite nanostructures in the vicinity of the cancer cells.

At 308, the portion of the composite nanostructures is irradiated with a stream of epithermal neutrons. For example, a focused beam of epithermal neutrons is directed to a location of the body of the patient where the cancer cells are located. The epithermal neutrons penetrate the body and irradiate the portion of the plurality of composite nanostructures accumulated in the vicinity of the cancer cells. The epithermal neutrons may react with the $^{10}$B in the composite nanostructures and cause generation of α particles according to the following equation:

While the low energy γ particles do not do much damage, the heavy α particles destroy the cancer cells locally. Beneficially, the heavy α particles have a penetration distance of only 1-2 cells, therefore limiting damage to healthy cells located in the proximity of the cancer cells. In some embodiments, a mass of $^{10}$B included in the plurality of composite nanostructures is in a range of 20-30 micrograms per gram of the cancer cells, which may generate sufficiently heavy α particles to destroy the cancer cells. In particular embodiments, the plurality of composite nanostructures may include $^{10}$B$_x$—Al$_y$O$_z$—Fe$_2$O$_3$ or $^{10}$B$_x$—Ti$_y$O$_z$—Fe$_2$O$_3$, where x>0, y>0, z>0, a>0 and b>0, or $^{10}$B$_x$—Al$_{2-x}$O$_3$-base material, where x is greater than 0 and less than 2, having 350-500 ppm Fe$_2$O$_3$ and 20-150 ppm boron.

Experimental Examples

Figure 4:
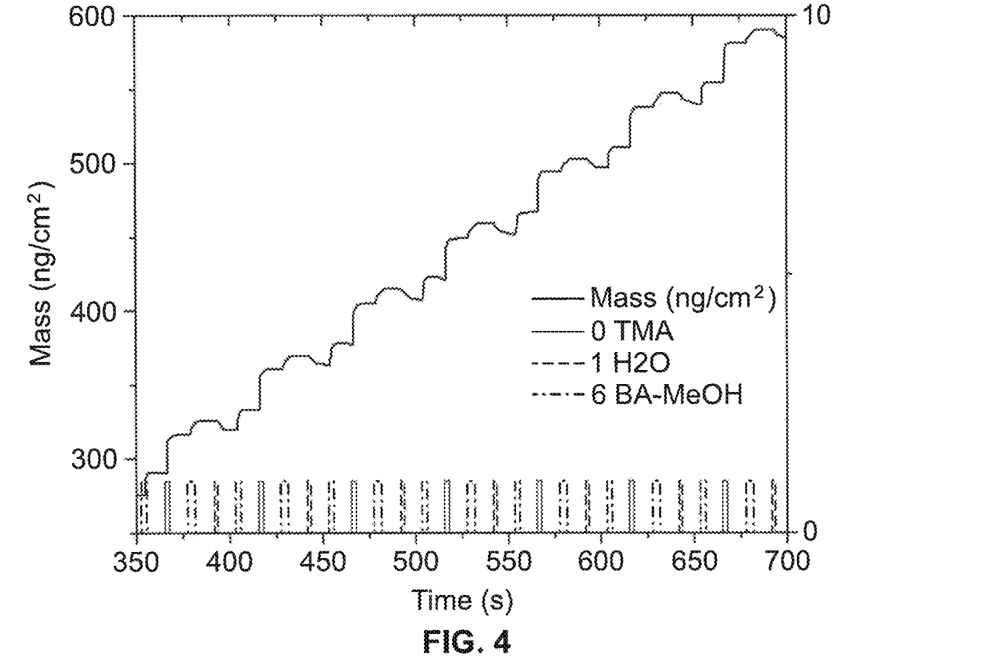
FIG. 4 shows a plot of Quartz Crystal Microbalance (QCM) measurements of mass deposition using ALD cycles of trimethyl aluminum (TMA), H$_2$O, and $^{10}$Boric Acid-Methanol ($^{10}$BA-Methanol) as a boron containing material to form a $^{10}$B—AlO composite structure.
Figure 5:
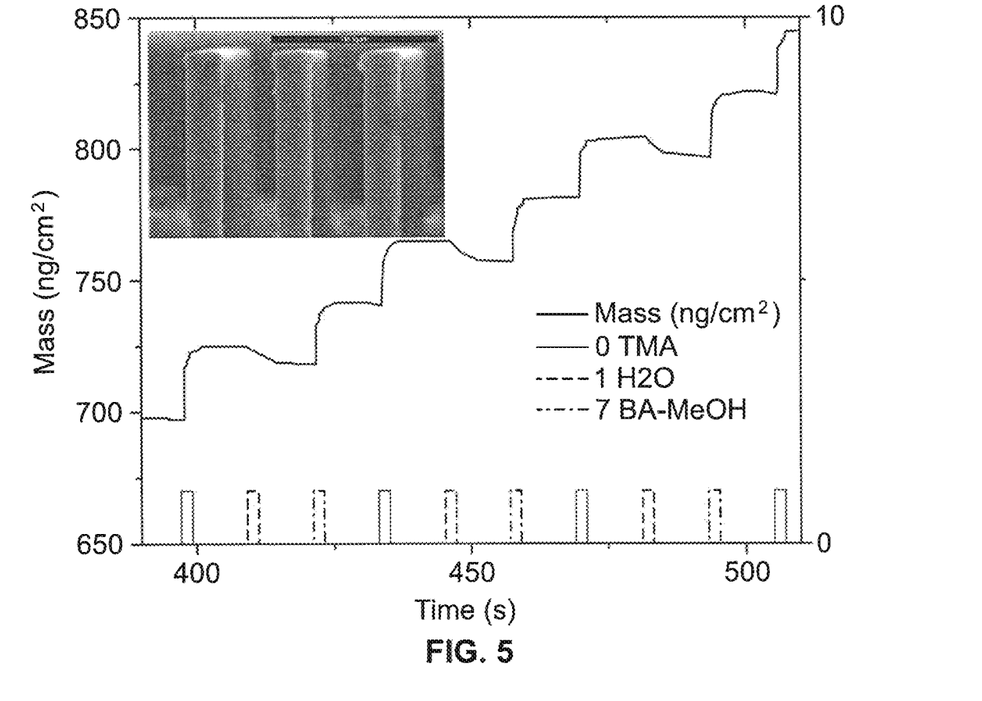
FIG. 5 shows a plot of QCM measurements of mass deposition using ALD cycles to form $^{10}$B—AlO—Si composite micropillars using trimethyl aluminum (TMA), H$_2$O, and $^{10}$B containing Trimethyl Borate (TMB); inset shows a scanning electron microscopy (SEM) image of the $^{10}$B—AlO—Si micropillars.

FIG. 4 shows a plot of Quartz Crystal Microbalance (QCM) measurements of mass deposition using ALD cycles to form a $^{10}$B—AlO composite structure using a boron containing precursor including $^{10}$Boric Acid-Methanol ($^{10}$BA-Methanol) on Si(100) wafer as the base material. TMA was used as an aluminum precursor and water was used as the oxygen containing precursor. Fast and linear controlled growth of $^{10}$B—AlO is demonstrated up to a mass of about 600 ng/cm$^2$. FIG. 5 shows a plot of QCM measurements of mass deposition using ALD cycles to form $^{10}$B—AlO films using a boron containing precursor including $^{10}$Trimethyl Borate($^{10}$TMB). Inset shows a scanning electron microscopy (SEM) image of the $^{10}$B—AlO deposited on Si micropillars to form $^{10}$B—AlO—Si composite micropillars. The micropillars are formed from Si(100) and serve as a substrate for deposition of the $^{10}$B—AlO composite thereon. Fast and linear controlled growth of $^{10}$B—AlO is demonstrated on the QCM surface up to a mass of about 850 ng/cm$^2$. Table I summarizes various ALD processes to generate $^{10}$B—AlO composite layers using $^{10}$BA-Methanol and $^{10}$TMB, and composition of these layers.

TABLE I

Composition of ¹⁰B-AlO layers formed using ALD with a ¹⁰BA-Methanol or TMB precursor.

| Sample | ALD Cycle | Thickness (nm) | O (atm. %) | Al (atm.%) | C (atm. %) | B (atm. %) |
|---|---|---|---|---|---|---|
| ¹⁰B-AlO layer formed with ALD cycles including ¹⁰BA-Methanol (¹⁰BAMeOH) boron containing precursor | | | | | | |
| 1 | TMA-N$_2$-BAMeOH-N$_2$-H$_2$O-N$_2$ | 24 | 56.35 | 29.09 | 4.49 | 10.07 |
| 2 | TMA-N$_2$-H$_2$O-N$_2$-BAMeOH-N$_2$ | 21 | 57.81 | 31.64 | 2.62 | 7.92 |
| 3 | TMA-N$_2$-BAMeOH-N$_2$ | 19 | 57 | 28.04 | 4.78 | 10.18 |
| ¹⁰B-AlO layer formed with ALD cycles including TMB boron containing precursor | | | | | | |
| 4 | TMA-N$_2$-H$_2$O-N$_2$-TMB-N$_2$ | 20 | 58.33 | 30.75 | 2.3 | 8.62 |
| 5 | TMA-N$_2$-H$_2$O-TMB-N$_2$ | 27 | 57.97 | 27.65 | 1.83 | 12.54 |

Figure 6A:
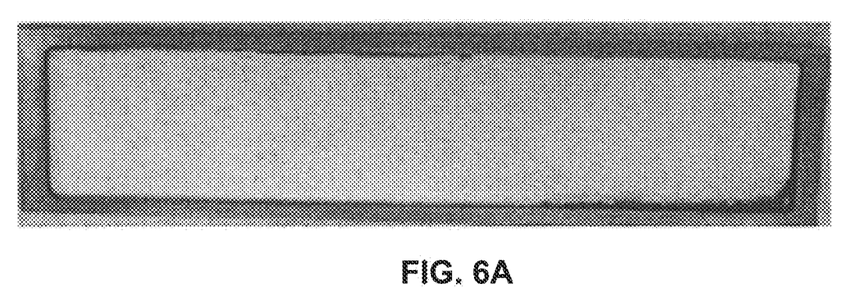
FIG. 6A is an optical image of Al$_2$O$_3$ nanoparticles.
Figure 6B:
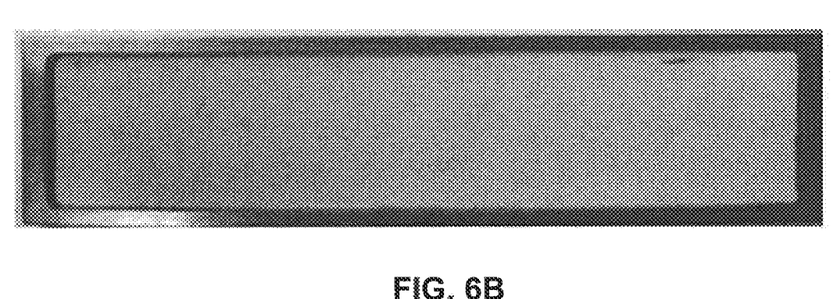
FIGS. 6B, 6C and 6D are optical images of the Al$_2$O$_3$ nanoparticles coated with iron oxide using progressive ALD cycles of ferrocene (Fe(Cp)$_2$) and O$_3$.
Figure 6C:
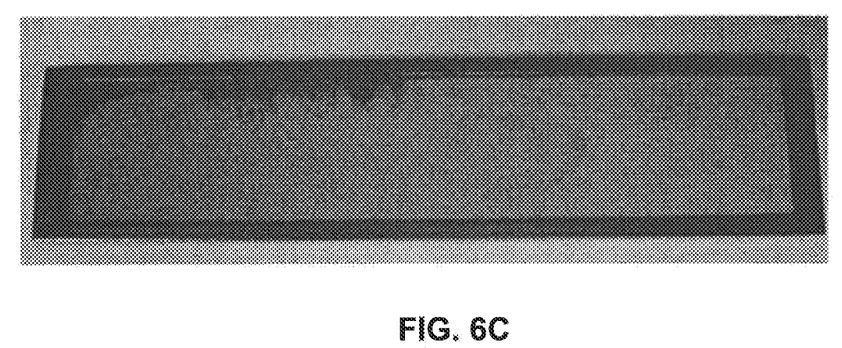
Figure 6D:
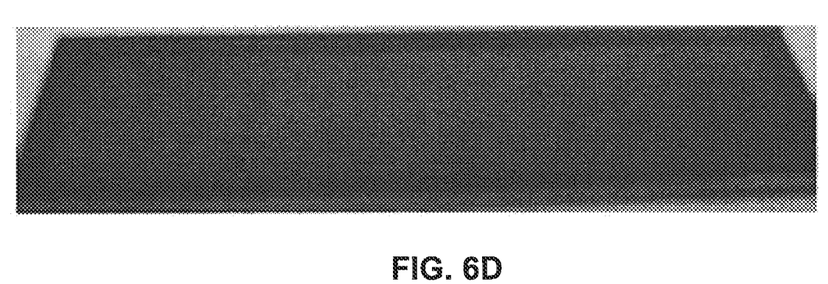
Figure 7A:
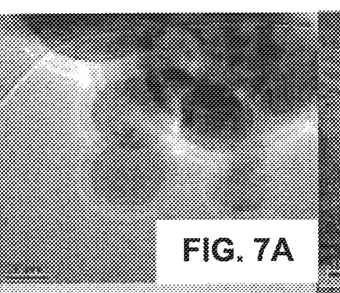
FIGS. 7A-7L are SEM images at various magnifications of the Fe$_2$O$_3$ coated Al$_2$O$_3$ nanoparticles formed using ALD.
Figure 7B:
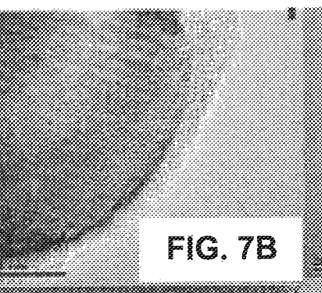
Figure 7C:
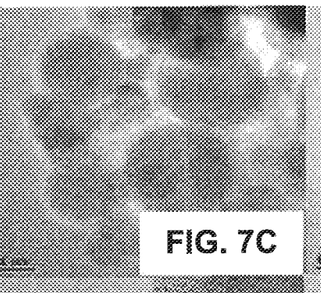
Figure 7D:
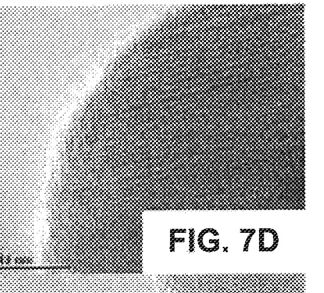
Figure 7E:
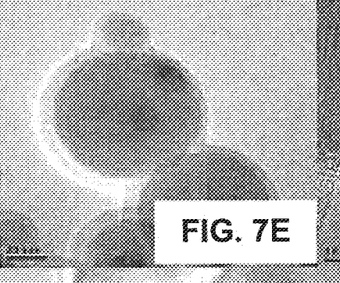
Figure 7F:
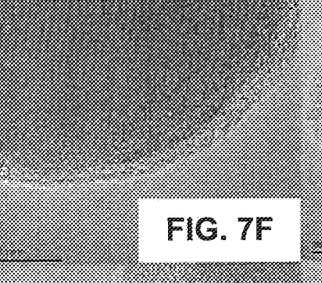
Figure 7G:
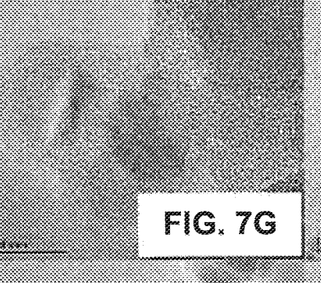
Figure 7H:
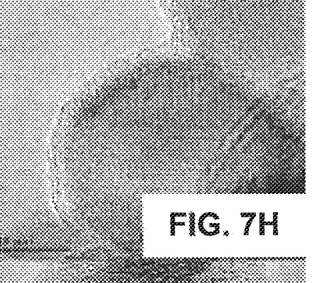
Figure 7I:
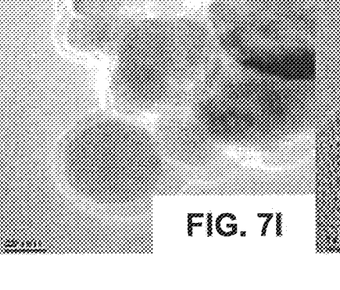
Figure 7J:
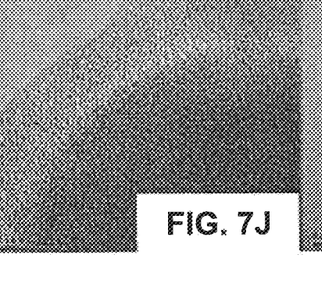
Figure 7K:
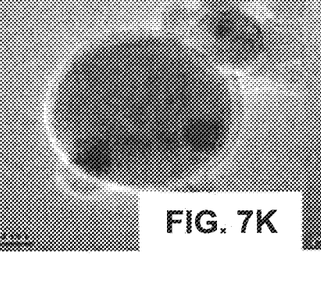
Figure 7L:
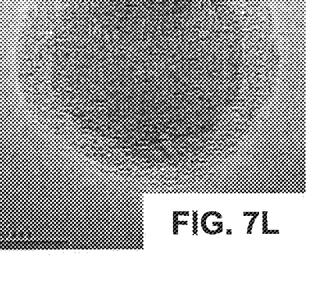

FIG. 6A is an optical image of Al$_2$O$_3$ nanoparticles; FIGS. 6B, 6C and 6D are optical images of the Al$_2$O$_3$ nanoparticles coated with iron oxide using progressive ALD cycles of Fe(Cp)$_2$ as an iron containing precursor and O$_3$ as an oxygen containing precursor so as to coat the Al$_2$O$_3$ nanoparticles with a layer of Fe$_2$O$_3$ and form magnetic nanoparticles. ALD can be used to control the thickness of the Fe$_2$O$_3$ layer on the Al$_2$O$_3$ base layer. FIGS. 7A-7L are SEM images at various magnifications of the Fe$_2$O$_3$ coated Al$_2$O$_3$ nanoparticles formed using the ALD process.

Figure 8A:
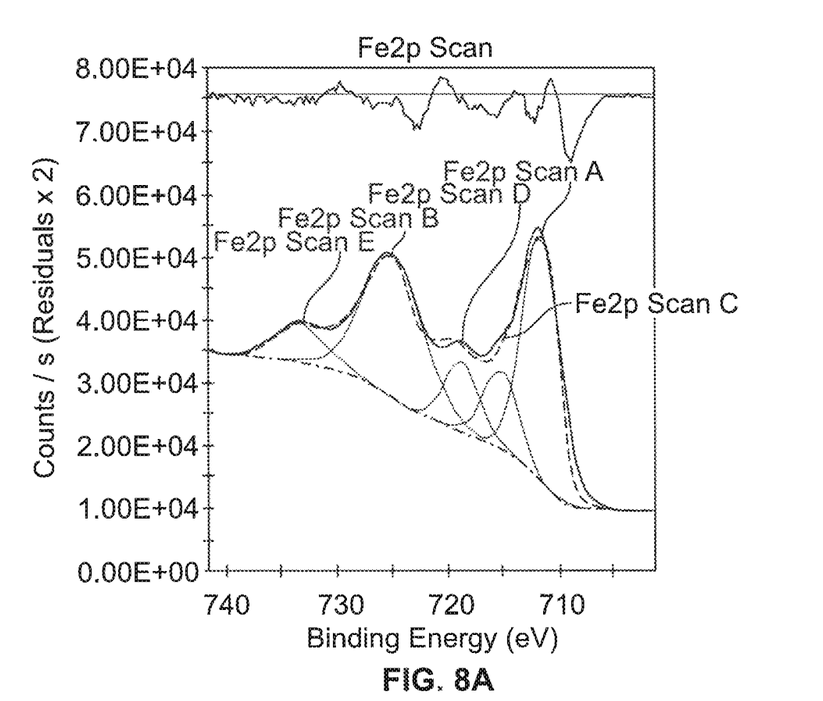
FIG. 8A is a X-ray Photon Spectroscopy (XPS) plot showing composition of commercially available Fe$_2$O$_3$ nanoparticles.
Figure 8B:
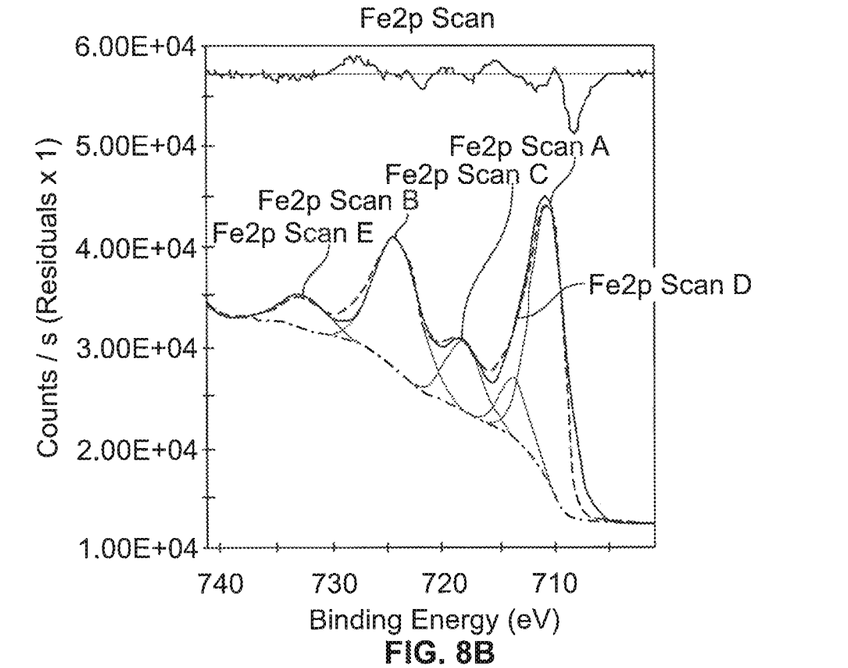
FIG. 8B is an XPS plot of composition of $^{10}$B—AlO—Fe$_2$O$_3$ composite nanostructures formed from the commercially available Fe$_2$O$_3$ nanoparticles using ALD.
Figure 9A:
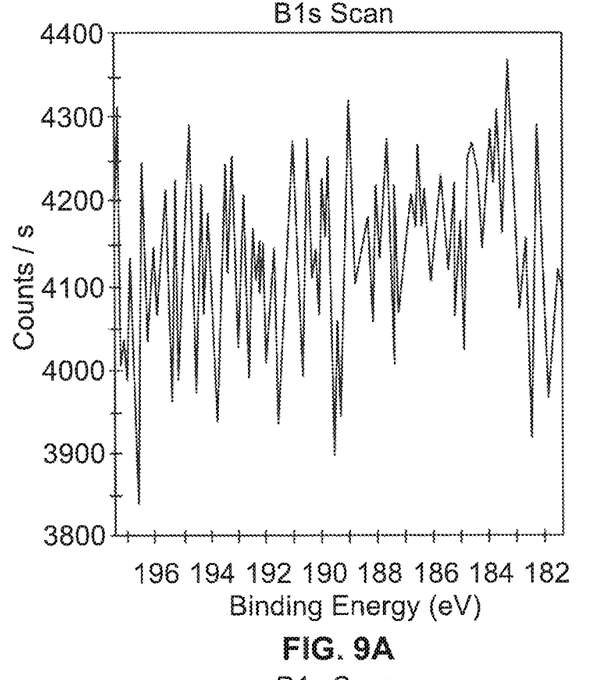
FIG. 9A is an XPS plot in the Boron spectrum of the commercially available Fe$_2$O$_3$ nanoparticles.
Figure 9B:
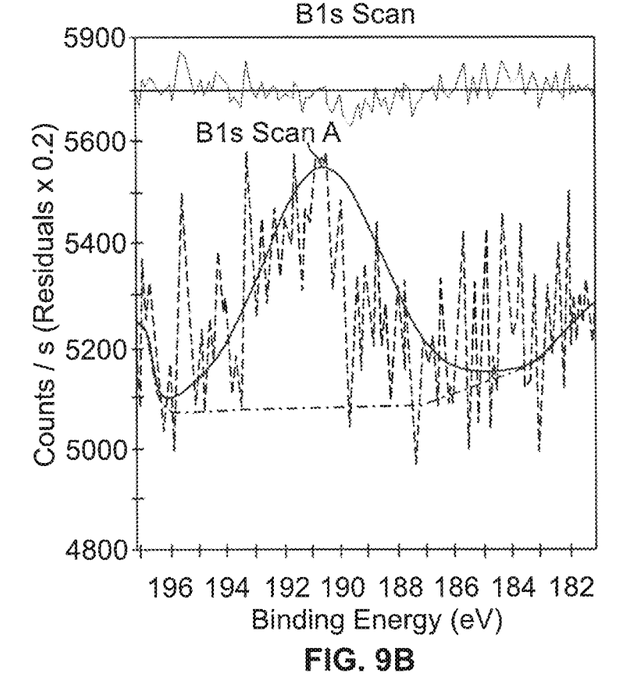
FIG. 9B is an XPS plot in the Boron spectrum of the $^{10}$B—AlO—Fe$_2$O$_3$ composite nanostructures.

FIG. 8A is an X-ray Photon Spectroscopy (XPS) plot showing composition of commercially available Fe$_2$O$_3$ nanoparticles, and FIG. 8B is an XPS plot of composition of B—AlO—Fe$_2$O$_3$ composite nanostructures formed from the commercially available Fe$_2$O$_3$ nanoparticles using ALD. The commercially available Fe$_2$O$_3$ particles had a diameter in a range of 20-40 nm. Thirty ALD cycles of TMA and ¹⁰BA-methanol were performed at 200 degrees Celsius to coat the Fe$_2$O$_3$ nanoparticles with about a 2.8 nm thick ¹⁰B—AlO layer to form ¹⁰B—AlO—Fe$_2$O$_3$ composite nanostructures. The ratio of Al to ¹⁰B was 3.1. FIG. 9A is an XPS plot in the Boron spectrum of the commercially available Fe$_2$O$_3$ nanoparticles, and FIG. 9B is an XPS plot in the Boron spectrum of the ¹⁰B—AlO—Fe$_2$O$_3$ composite nanostructures. A visible ¹⁰B peak is observed after performing the ¹⁰B—AlO ALD on the Fe$_2$O$_3$ nanoparticles. Table II summarizes composition of the commercially available Fe$_2$O$_3$ nanoparticles before and after the ALD process.

TABLE II

Composition of commercially available Fe$_2$O$_3$ nanoparticles and ¹⁰B—AlO—Fe$_2$O$_3$ composite nanostructures formed therefrom using ALD.

| | Element | Atomic % |
|---|---|---|
| Fe$_2$O$_3$ | Al | 0 |
| | B | 0 |
| | C | 4.16 |
| | O | 57.64 |
| | Fe | 38.2 |
| ¹⁰B—AlO—Fe$_2$O$_3$ | Al | 13.85 |
| | B | 4.41 |
| | C | 4.86 |
| | O | 62.45 |
| | Fe | 14.41 |

Figure 10:
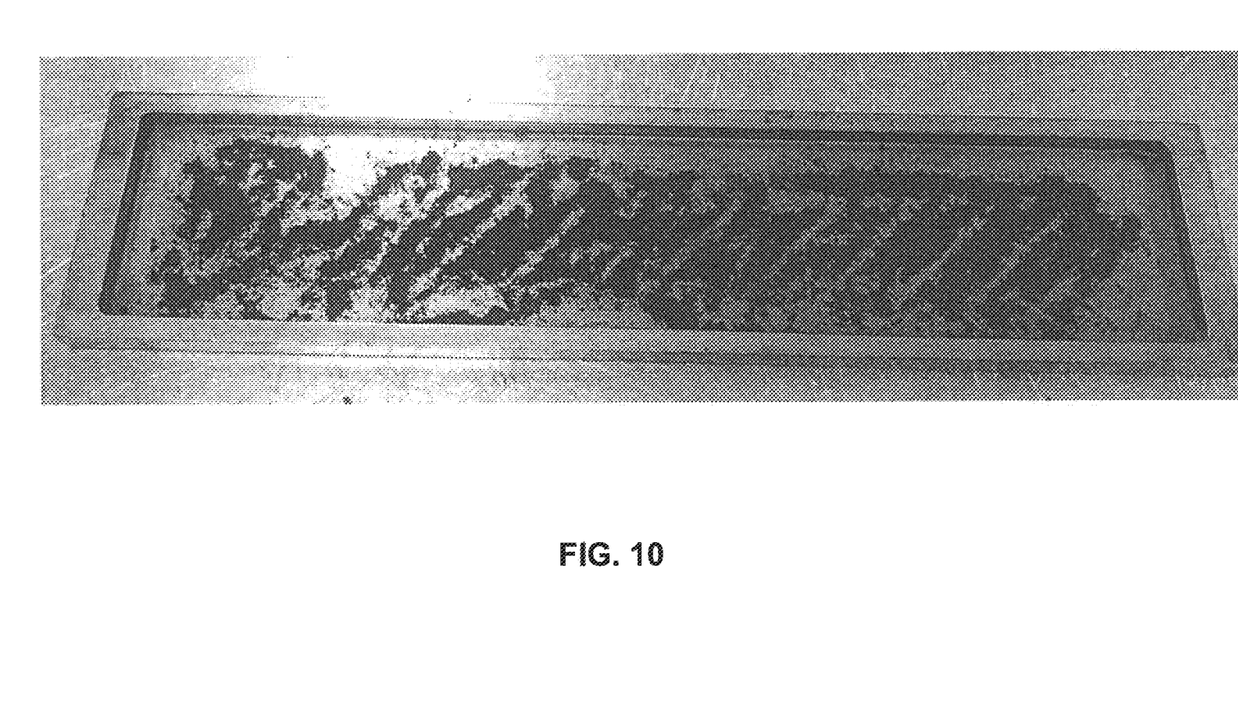
FIG. 10 is an optical image of $^{10}$B—AlO—Fe$_2$O$_3$ composite nanostructures.
Figure 11A:
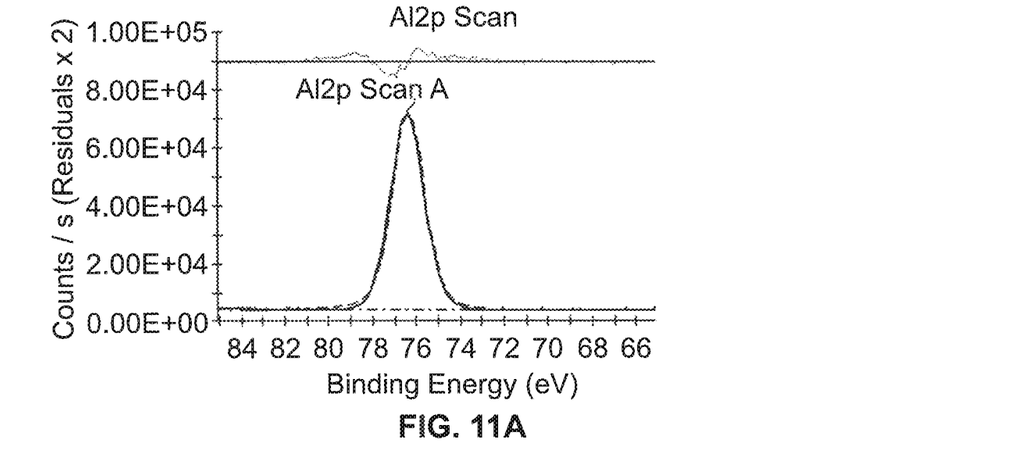
FIGS. 11A, 11B and 11C are XPS scans in the aluminum, boron and oxygen spectrums, respectively of the $^{10}$B—AlO—Si composite nanostructures.
Figure 11B:
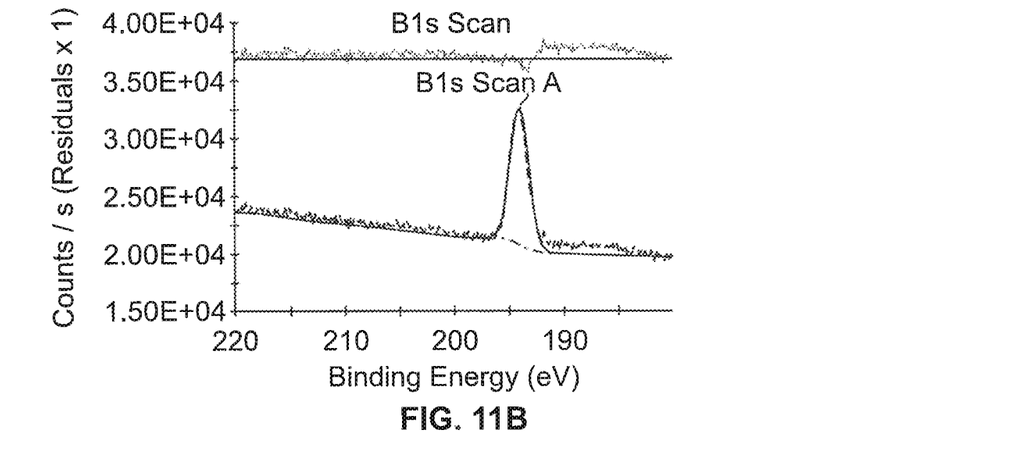
Figure 11C:
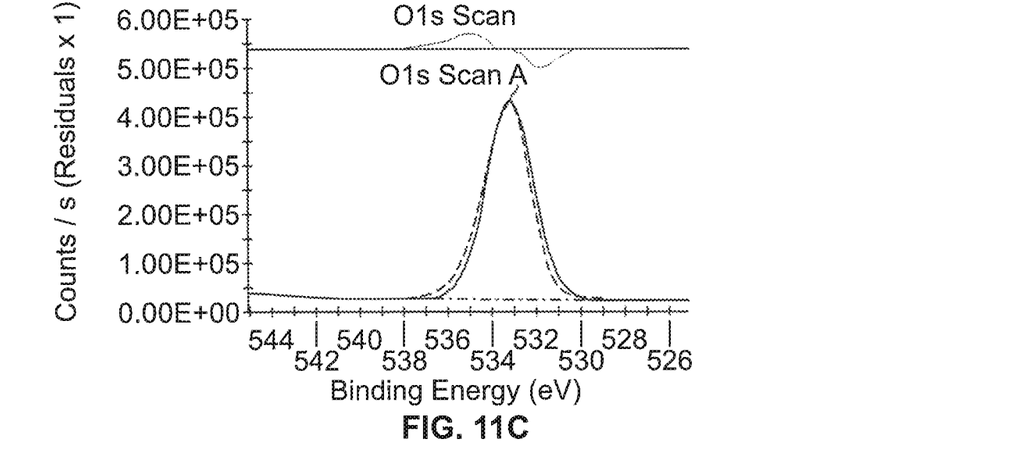
Figure 12A:
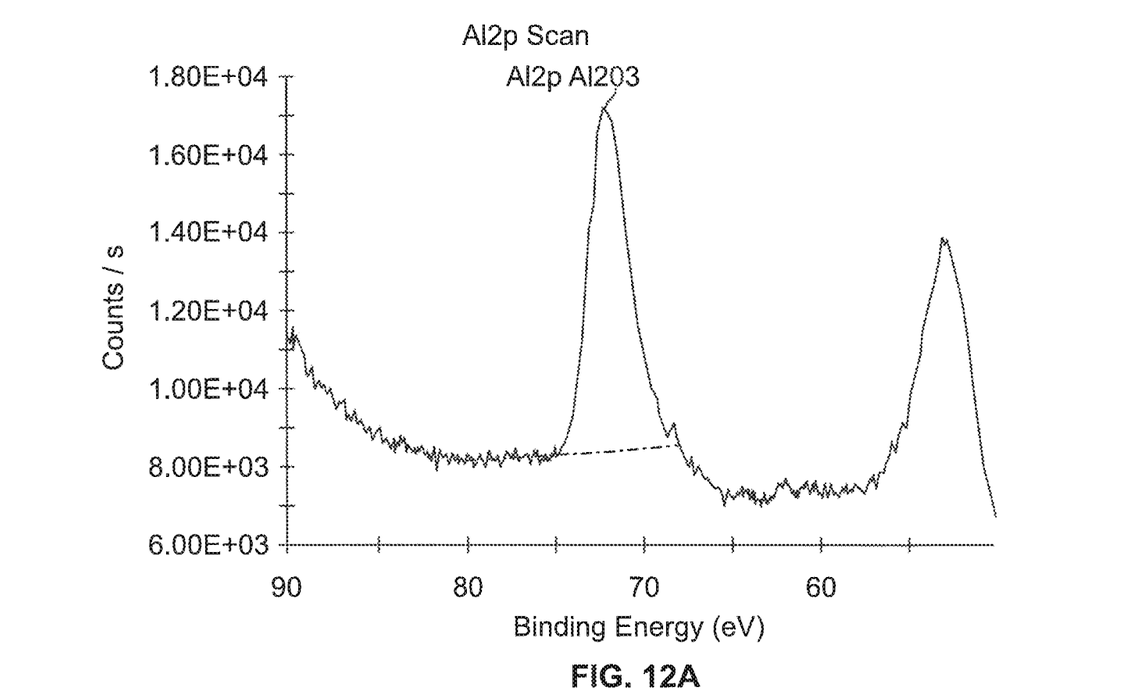
FIGS. 12A, 12B, 12C and 12D are XPS scans in the aluminum, boron, oxygen and iron spectrums, respectively of the $^{10}$B—AlO—Fe$_2$O$_3$ composite nanostructures of FIG. 10.
Figure 12B:
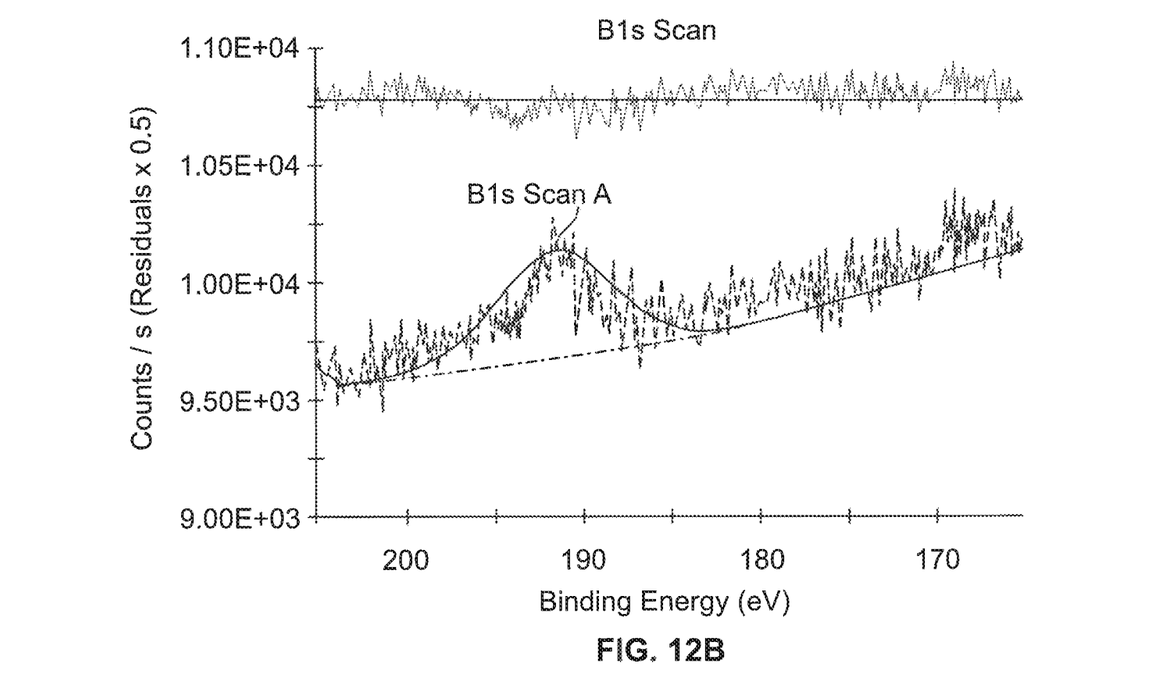
Figure 12C:
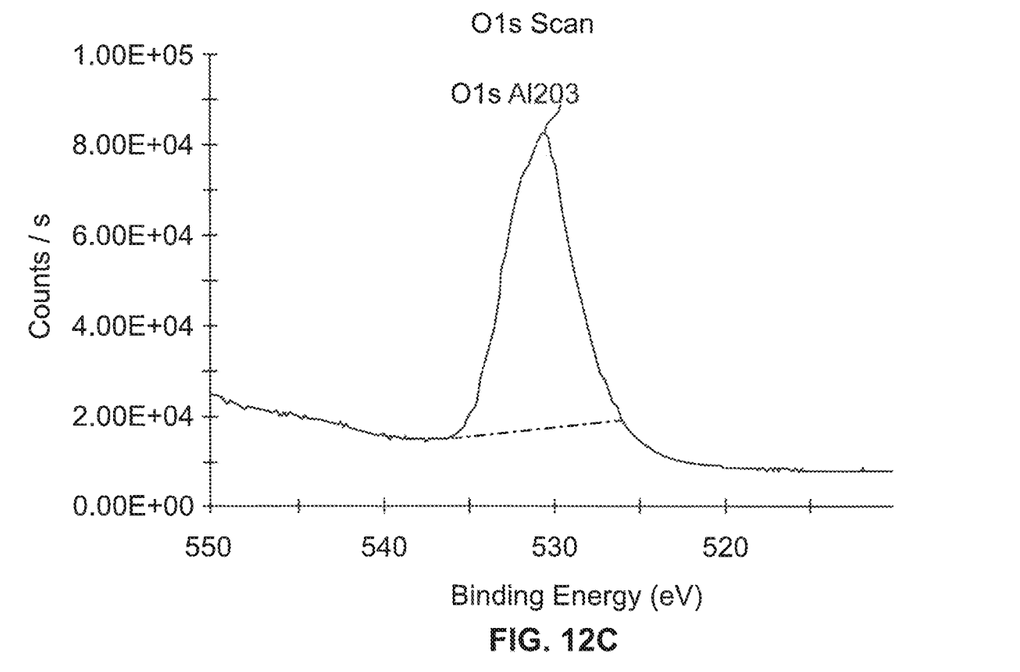
Figure 12D:
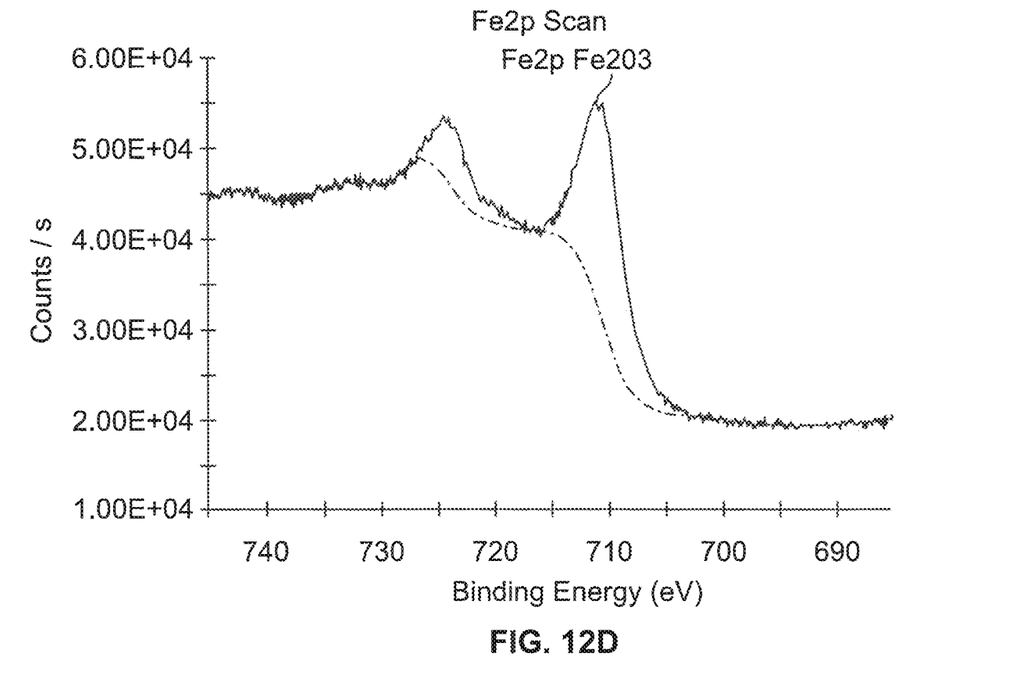

FIG. 10 is an optical image of ¹⁰B—AlO—Fe$_2$O$_3$ composite nanostructures formed by performing a 2 second TMA exposure, a 20 second N$_2$ purge, a 2 second ¹⁰B A-MeOH exposure and a 20 second N$_2$ purge. A total of 50 cycles were performed obtain an about 5 nm thick ¹⁰B—AlO layer on the Fe$_2$O$_3$ nanoparticles as observed on a Si monitor wafer present in the reaction chamber during the ALD process. FIGS. 11A, 11B and 11C are XPS scans in the aluminum, boron and oxygen spectrums, respectively of the B—AlO—Si composite nanostructures. FIGS. 12A, 12B, 12C and 12D are XPS scans in the aluminum, boron, oxygen and iron spectrums, respectively of the B—AlO—Fe$_2$O$_3$ composite nanostructures of FIG. 10. ¹⁰B peaks are clearly observed in FIGS. 11B and 12B.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any embodiments or of what may be claimed, but rather as descriptions of features specific to particular implementations of particular embodiments. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method, comprising:
    providing a plurality of nanostructures comprising a base material comprising $Fe_2O_3$;
    exposing the plurality of nanostructures to a first material comprising trimethylaluminum $(Al(CH_3)_3)$ (TMA) at a first deposition temperature in the range of 100° C. to 300° C.;
    exposing the plurality of nanostructures to a second material at a second deposition temperature in the range of 100° C. to 300° C.; and
    exposing the plurality of nanostructures to a Boron-10 ($^{10}B$) containing material comprising trimethyl borate (TMB) at a third deposition temperature in the range of 100° C. to 300° C. so as to form $^{10}B$-metal oxide composite nanostructures comprising an atomic percent concentration of oxygen in the range of 50 atomic % to 60 atomic % and an atomic percentage of aluminum in the range of 25 atomic % to 40 atomic %.

2. The method of claim 1, wherein the $^{10}B$-metal oxide composite nanostructure comprises $^{10}B_x$—$Al_yO_z$—$Fe_2O_3$, where x>0, y>0 and z>0.

3. The method of claim 1, wherein providing the plurality of nanostructures comprises:
    exposing a plurality of nanoparticles to a first base material precursor at a fourth deposition temperature; and
    exposing the plurality of nanoparticles to a second base material precursor at a fifth deposition temperature,
    wherein a layer of the base material is deposited on each of the plurality of nanoparticles.

4. The method of claim 1, wherein the $^{10}B$-metal oxide composite nanostructures comprising an atomic percent concentration of boron in the range of 1 atomic % to 10 atomic %.

* * * * *